(12) United States Patent
Schawe (10) Patent No.: US 9,816,907 B2
(45) Date of Patent: Nov. 14, 2017

(54) TEMPERATURE MODULATED THERMOGRAVIMETRIC ANALYSIS

(71) Applicant: Mettler-Toledo AG, Greifensee (CH)

(72) Inventor: Jürgen Schawe, Uster (CH)

(73) Assignee: Mettler-Toledo GmbH, Greifensee (CH)

( * ) Notice: Subject to any disclaimer, the term of this patent is extended or adjusted under 35 U.S.C. 154(b) by 331 days.

(21) Appl. No.: 14/705,612

(22) Filed: May 6, 2015

(65) Prior Publication Data
US 2015/0323438 A1    Nov. 12, 2015

(30) Foreign Application Priority Data

May 6, 2014    (EP) .................................. 14167177

(51) Int. Cl.
*G01N 5/04* (2006.01)
*G01N 25/00* (2006.01)
*G01G 7/00* (2006.01)

(52) U.S. Cl.
CPC .................. *G01N 5/04* (2013.01); *G01G 7/00* (2013.01); *G01N 25/00* (2013.01)

(58) Field of Classification Search
CPC ..................................................... G01K 7/02; G01K 7/22; G01K 13/02; G01K 2205/04; G01K 2013/024; H01R 4/023; H01R 4/029; H01R 43/28; H02M 1/32; H02M 1/38; H02M 1/53806; H01C 7/008; H01C 17/00; G01N 5/04; G01N 25/00; B23K 31/02
See application file for complete search history.

(56) References Cited

U.S. PATENT DOCUMENTS 3,902,354 A * 9/1975 Harlan .................. G01K 1/045
374/14
5,055,264 A * 10/1991 Czarnecki ................ G01N 5/04
374/14
(Continued)

OTHER PUBLICATIONS

Blaine, R.L. et al., Obtaining Kinetic Parameters By Modulated Thermogravimetry, Journal of Thermal Analysis, 1998, pp. 695-704, 54.

(Continued)

*Primary Examiner* — Manish S Shah
(74) *Attorney, Agent, or Firm* — Standley Law Group LLP (57) ABSTRACT

A sample is analyzed by temperature-modulated thermogravimetric analysis (TMTGA), using a thermogravimetric analysis (TGA) instrument. The TGA instrument comprises a furnace arranged in a furnace housing and an electronic balance with a load receiver arranged in a balance housing, wherein the load receiver extends into the furnace housing. A measuring position is arranged at one end of the load receiver within the furnace housing. A control unit controls the balance and/or the furnace. The TMTGA method includes at least using the TGA instrument to subject the sample to a temperature program that varies the temperature of the furnace and provides temperature-time setpoints for controlling the sample temperature, measuring the mass change of the sample as a function of time, and determining at least one kinetic parameter of the sample based on mass change. The temperature program may be stochastic and/or event-controlled in nature.

21 Claims, 4 Drawing Sheets

(56) References Cited

U.S. PATENT DOCUMENTS

| | | | |
|---|---|---|---|
| 5,165,792 A | 11/1992 | Crowe et al. | |
| 6,113,261 A | 9/2000 | Blaine | |
| 6,336,741 B1 | 1/2002 | Blaine | |
| 6,551,835 B1 | 4/2003 | Schawe et al. | |
| 2006/0120431 A1* | 6/2006 | Monceau | G01N 5/04 |
| | | | 374/14 |
| 2006/0140246 A1* | 6/2006 | Danley | G01G 19/52 |
| | | | 374/14 |

OTHER PUBLICATIONS

Blaine, R.L., Obtaining Kinetic Parameters Using Modulated Temperature, ASTM Special Technical Publication, 2001, pp. 115-128, 1402.

Dickens, B., Automation of Factor-Jump Thermogravimetry for Active Computer Control, Thermochimica Acta, 1979, pp. 41-56, 29.

Fraga, I. et al., TOPEM, A New Temperature Modulated DSC Technique, Application to the glass transition of polymers, Journal of Thermal Analysis and Calorimetry, 2007, pp. 119-124, 87.

Schawe, J.E.K. et al., Stochastic temperature modulation: A new technique in temperature-modulated DSC, Thermochimica Acta, 2006, pp. 147-155, 446.

* cited by examiner

TEMPERATURE MODULATED THERMOGRAVIMETRIC ANALYSIS

CROSS-REFERENCE TO RELATED APPLICATIONS

This application is entitled to benefit of a right of priority under 35 USC §119 from European patent application 14167177.6, filed on 6 May 2014, the content of which is incorporated by reference as if fully recited herein.

TECHNICAL FIELD

The disclosed invention relates to a simplified, robust technique for evaluating thermogravimetric measurements as well as to a thermogravimetric analysis instrument utilizing this technique.

BACKGROUND OF THE ART

Thermogravimetric analysis (TGA) is a thermoanalytical technique which measures the change in mass (gains and losses) of a sample as a function of temperature and time. TGA experiments are usually performed by measuring the mass of a sample which is subjected to a temperature program. Known TGA temperature programs can be isothermal, can have a constant heating rate or the heating rate can be related to a function of the mass change. The last temperature program is e.g. realized in TGA instruments by Mettler-Toledo. TGA measurements can provide information about the sample material's properties, such as its thermal stability, as well as its composition.

An approach first introduced in 1969 by Flynn to derive kinetic data from thermogravimetric measurements (J H Flynn, The historical development of applied nonisothermal kinetics, in: Schwenker, R F, Garn, P D (Eds.), Thermal Analysis, Vol. 2, New York: Academic Press; 1969: 1111-1126) was a temperature modulated thermogravimetric analysis (TMTGA) method, which comprised subjecting the sample to a program with a sinusoidal or step-wise temperature change. The temperature program for a TMTGA experiment comprises a temperature with a modulation amplitude $T_a$ and allows to derive kinetic data, such as the average apparent activation energy $E_\alpha$, from the resulting TMTGA curves. The apparent activation energy $E_\alpha$ of a sample is an important parameter, which is characteristic for said sample, its purity and quality.

$E_\alpha$ can be derived in the temperature interval of the modulation amplitude $T_a$ based on the isoconversion principle, as $$\frac{E_\alpha}{R} = \frac{\ln r(T_1) - \ln r(T_2)}{T_2^{-1} - T_1^{-1}} \quad (1)$$

with $r := d\alpha/dt$, where $E_\alpha$ is the average apparent activation energy of the conversion $\alpha$ between the temperatures $T_1$ and $T_2$ and $r(T_i)$ is the reaction rate at the temperature $T_i$. This equation may be considered as being independent of the kind of reaction taking place while the sample is subjected to the temperature program and could therefore be described as being model independent, at least as long as no specific model is selected. The reaction taking place while the sample is subjected to the temperature program will from now on be referred to as "reaction" for ease of reading.

Temperature $T_1$ represents the maximum and temperature $T_2$ the minimum temperature of the temperature modulation. Taking T as the average temperature it follows that $T_1 = T + T_a$ and $T_2 = T - T_a$.

U.S. Pat. No. 6,113,261 A and U.S. Pat. No. 6,336,741 B1 disclose a similar approach to a TMTGA method which utilizes a periodic temperature modulation, such as e.g. a sinusoidal modulation, superimposed on a linear temperature program. The apparent activation energy is here determined as $$E_\alpha = R \frac{(T^2 - T_a^2)}{2T_a} \ln \frac{r(T_1)}{r(T_2)} \quad (2)$$

with equation (2) being a simple arithmetic rearrangement of Equation (1). A large mass loss or decrease during a single modulation cycle at fast reaction rates generates non-linear effects and additionally numerical errors for the determination of $\ln r(T_1) - \ln r(T_2)$. Therefore, the measurements are performed in such a way that the underlying heating due to the linear temperature program can be neglected during a period of modulation, as the temperature modulation amplitude $T_a$ is selected as being so small that the measured signal can be described by linear response theory and be separated by Fourier analysis.

A main drawback of the currently known TMTGA setups is that these are limited to the application of periodic temperature modulations. This becomes particularly evident when applying these periodic TMTGA methods to reactions, which show only low sensitivity and therefore low intensities of the reaction rate r(t) at the beginning or near the end of a reaction. Low intensities in combination with low reaction rates dramatically increase the noise in the numerical results. Further a large mass decrease during a single modulation cycle can occur near the maximum reaction rate, which can cause numerical errors and a lack of data due to a large conversion within one period of the modulated temperature.

Therefore, it would be advantageous to develop a temperature modulated thermogravimetric analysis (TMTGA) method which is more generally applicable and robust with regard to experimental uncertainties and in particular not limited to a periodic temperature modulation.

SUMMARY

Such a TMTGA method for analyzing a sample comprises several steps. The sample is placed on a measurement position in a thermogravimetric analysis (TGA) instrument, which TGA instrument comprises a furnace arranged in a furnace housing, an electronic balance with a load receiver arranged in a balance housing, wherein the load receiver extends into the furnace housing, wherein said measuring position is arranged at one end of the load receiver within the furnace housing, and a control unit for controlling the balance and/or the furnace. Said sample is then subjecting to a temperature program provided by the control unit, which varies the temperature of the furnace, and the mass change (m(T,t)) of said sample is measured with the electronic balance while the sample is being subjected to said temperature program as a function of time. At least one kinetic parameter of the sample can be determined by analyzing said mass changes. The temperature program (T(t)) used for the TMTGA method is preferably a stochastic and/or event-controlled temperature program providing temperature-time setpoints for controlling the sample temperature and comprising an underlying temperature change ($\overline{T}(t)$) superimposed by a temperature perturbation ($\delta T(t)$) with a characteristic time of modulation ($\tau$) according to $T(t)=\overline{T}(t)+\delta T(t)$.

Using a stochastic and/or event-controlled temperature program has the advantage that the course of the modulation function rather than only its intensities can be analyzed. The large number of available data used for the analysis significantly enhances the accuracy of the results.

The method can further comprise the step of determining the sample temperature as a function of time with a temperature sensor arranged in the vicinity of measurement position and/or the sample. Knowledge of the actual sample temperature as a function of time can be used to enhance the determination of the at least one kinetic parameter of the sample. Further the actual sample temperature can be used to control the application of the temperature program to the sample by controlling the furnace temperature to ensure that the sample temperature closely follows the temperature setpoints provided by the temperature program.

For an embodiment the characteristic time of modulation of the stochastic temperature perturbation fluctuates randomly.

The stochastic temperature perturbation may comprise pulse sequences, each pulse sequence having a pulse length representing the characteristic time of modulation ($\tau$), wherein a random number generator generates the pulse lengths of the pulses between two given limits ($\tau_{min}, \tau_{max}$).

Another example for a stochastic temperature perturbation may comprise varying the intensity ($T_a$) of the stochastic temperature perturbation.

A further embodiment of the TMTGA method comprises said event-controlled temperature perturbation which may be modulated by modulating the characteristic time of modulation ($\tau$) and/or the temperature modulation intensity ($T_a$) in relation to changes of the mass (dm/dt), the conversion ($\alpha$) and/or its derivatives during a TGA experiment.

Here a thermal event taking place within the sample influences the temperature perturbation applied to the sample and e.g. adapts the modulation time of the temperature perturbation in such a way that the modulation time is longer while the sample reaction shows a low reaction rate and shorter while the reaction shows a high reaction rate.

In a further embodiment said stochastic and/or event-controlled temperature perturbation may further comprise adapting the underlying heating rate ($\overline{\beta}$) of the temperature program.

In a further embodiment the stochastic and/or event-controlled temperature program may further provide non-periodic temperature-time data for controlling the sample temperature. Non-periodic temperature-time data or setpoints enable the analysis of the sample without being restricted to selective excitations of the thermal events within the sample.

In a further embodiment the kinetic parameter may be determined from the mass change of the sample as a function of time and temperature (m(t,T)) being measured in a single TGA measurement. This is advantageous as the measurement only requires a small amount of sample and can even be applied to e.g. experimental samples which only exist or can only be produced in very small amounts as well as to rare or precious samples.

In a further embodiment said TMTGA method further comprises determining the parameters of the temperature perturbation ($\delta T(t)$) from a TGA test-measurement of the sample, followed by performing a TMTGA measurement by measuring at least one like sample with the TGA instrument using a temperature program comprising said temperature perturbation with said previously determined parameters and determining at least one kinetic parameter of the sample from said TMTGA measurement. This is advantageous for measuring recurring samples e.g. within a process or production environment as a TMTGA method for a specific sample type can be developed and used for future sample of that sample type.

Preferably the apparent activation energy ($E_\alpha$) is determined with said method as kinetic parameter of a sample. The apparent activation energy of a sample is an important parameter which is characteristic for said sample, its purity and quality.

Another aspect relates to a thermogravimetric analysis (TGA) instrument for carrying out said method described above. Said TGA instrument comprises a furnace arranged in a furnace housing, an electronic balance with a load receiver arranged in a balance housing, wherein the load receiver extends into the furnace housing and comprises a measuring position for receiving a sample arranged at one end of the load receiver within the furnace housing, a control unit for controlling the balance and/or the furnace comprising a temperature program which controls the temperature of the furnace, wherein the electronic balance measures changes in the mass of the sample as a function of time and temperature, while the sample is being subjected to the temperature program, and wherein the control unit further comprises means to determine at least one kinetic parameter of the sample by analyzing the sample's changes in mass over time and temperature. The temperature program (T(t)) is a stochastic and/or event-controlled temperature program providing temperature-time setpoints for controlling the sample temperature and comprises an underlying temperature change ($\overline{T}(t)$) superimposed by a temperature perturbation ($\delta T(t)$) with a characteristic time of modulation ($\tau$) according to $$T(t)=\overline{T}(t)+\delta T(t).$$

Preferably a temperature sensor is arranged in the vicinity of the measurement position to measure the sample temperature. Thereby the actual sample temperature can be monitored and not only the temperature of the furnace, which allows a more precise temperature control of the sample when being subjected to said temperature program.

The at least one kinetic parameter is preferably the apparent activation energy ($E_\alpha$) of said sample.

BRIEF DESCRIPTION OF THE DRAWINGS

The invention is described in more detail below with reference to the following Figures, wherein identical elements carry the same or similar reference symbols. The Figures show.

DETAILED DESCRIPTION OF EXEMPLARY EMBODIMENTS

Figure 1:
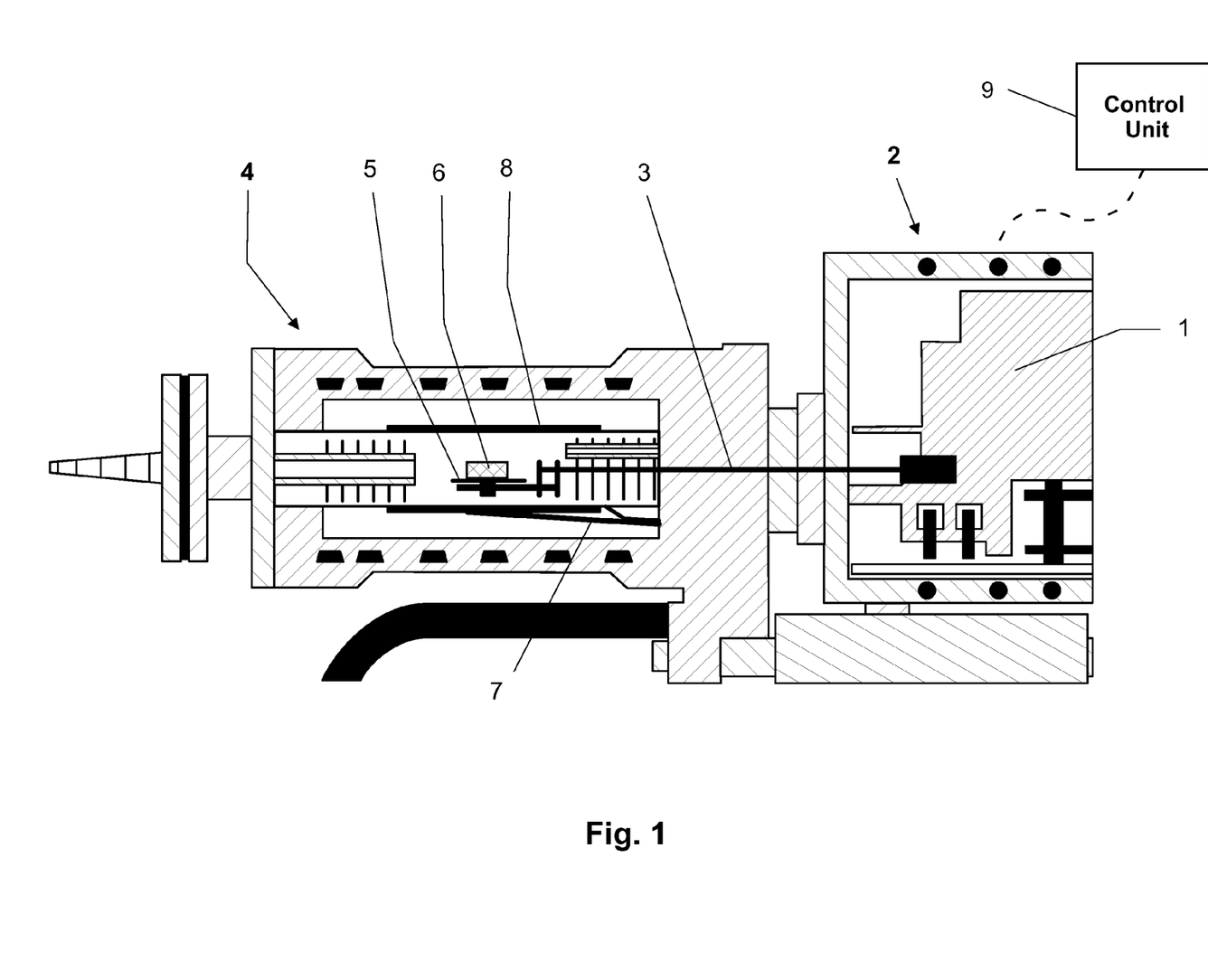
FIG. 1 which is a Schematic setup of a TGA instrument utilizing the inventive TMTGA method.

FIG. 1 shows schematically a setup of a TGA instrument comprising an electronic balance 1 arranged in a balance housing 2 and comprising a load receiver 3 reaching into a furnace housing 4. The TGA instrument further comprises a control unit 9 (only indicated here) for controlling the furnace and/or the electronic balance. TGA instruments are well known in the art, and are described here only in an overview sense. TGA instruments are e.g. available from Mettler-Toledo.

The load receiver 3 can comprise at least one measurement position arranged at the end of the load receiver 3 arranged in the furnace housing 4 or a TGA sensor 5 comprising at least one measurement position may be connected to said end of the load receiver 3, as shown here. At least one sample 6 can be arranged on said at least one measurement position within the furnace housing 4. The sample 6 can be either arranged directly on the measurement position or can be contained in a suitable crucible. The balance housing 2 is essentially thermally isolated from the furnace housing 4. The TGA sensor 5 is arranged in the furnace housing 4 within a furnace 8 comprising a heater for applying heat according to a temperature program to the sample 6. The temperature of the furnace 8, which is controlled by the control unit 9, can be detected by a temperature sensor 7. The instrument may further comprise at least a further temperature sensor in the vicinity of and preferably in contact with a measurement position for detecting the actual temperature of the sample. The temperature sensor measuring the sample temperature can e.g. be attached to or be part of the TGA sensor 5 (as shown here).

Measurements are performed by placing at least one sample 6 on the at least one measurement position within the furnace housing 4 and subjecting the sample 6 to a temperature program generated by the heater of the furnace 8. Any mass change of the sample 6 is then detected by the balance 1. The results can e.g. be displayed in a mass-temperature diagram.

The sample mass m in a TGA experiment can be described by $$m = m_0(1 - \Delta\mu_r \alpha(T,t)) \quad (3)$$

where $m_0$ is the initial mass, $\alpha(T,t)$ the conversion of the reaction as a function of temperature and time and $\Delta\mu_r = \Delta m/m_0$ the specific mass change during the reaction of investigation. The overall mass change during the reaction is $\Delta m$, with $\Delta m$, $\Delta\mu_r < 0$ when the sample mass is reduced during the reaction and consequently $\Delta m$, $\Delta\mu_r > 0$ when the sample mass is increased during the reaction.

The time derivative of equation (3) is known as the DTG curve:

$$\frac{dm}{dt} = -m_0 \Delta\mu_r r(T, t) \quad (4)$$

with $r := d\alpha/dt$ as reaction rate.

A modulated temperature program T(t) suitable for TMTGA experiments according to the invention comprises a low underlying heating rate $\bar{\beta}$ superimposed by a sufficiently small temperature perturbation $\delta T(t)$. Said modulated temperature program T(t) can be expressed as:

$$T(t) = \bar{T}(t) + \delta T(t) = T_0 + \bar{\beta}t + \delta T(t) \quad (5)$$

where $T_0$ is the start temperature at the begin of the measurement and $\bar{T}(t)$ the underlying temperature.

An instrument suitable for TMTGA experiments may further comprise means to apply said modulated temperature as modulated temperature program to the sample and the instrument may further comprises means for detecting and analyzing the resulting TGA and/or TMTGA curves.

The temperature dependence of the reaction rate r(T,t) (see Equation (4)) can be expressed by a Taylor expansion around $\bar{T}$ as $$\frac{dm}{dt} = m_0 \cdot \Delta\mu_r \left( r(\bar{T}, t) + \left(\frac{\partial r}{\partial T}\right)_{\bar{T}} \delta T(t) \right) \quad (6)$$

where $(\partial r/\partial T)_{\bar{T}}$ is the temperature derivative of the reaction rate r at the underlying temperature $\bar{T}$.

The temperature perturbation $\delta T(t)$ can be expressed by an arbitrary modulation function y(t):

$$\delta T(t) = T_a \cdot y(t) \quad (7)$$

where $T_a$ is the intensity of the perturbation.

In the following it will be shown that principally any periodical or non-periodic function can be used as modulation function y(t). Examples for periodic functions include besides others sinusoidal, box, triangular and saw-tooth functions.

Examples for non-periodic modulation functions y(t) comprise stochastic modulation functions, such as stochastic pulse sequences. Stochastic pulse sequences are for example disclosed in relation to temperature modulated differential scanning calorimetry (TMDSC) in U.S. Pat. No. 6,551,835 B1 and JEK Schawe, et al., Stochastic temperature modulation: A new technique in temperature-modulated DSC, Thermochim. Acta 2006, 446: 147-155.

Particularly advantageous is the use of event-controlled modulated functions y(t), which behavior is controlled by the thermal events taking place in the sample subjected to a modulated temperature program.

The total mass loss rate dm/dt of the TMTGA experiment can be derived from Equations (6) and (7) as:

$$\frac{dm}{dt} = m_0 \Delta\mu_r \left( r(\bar{T}, t) + \left(\frac{\partial r}{\partial T}\right)_{\bar{T}} T_a y(t) \right) = \overline{\left(\frac{dm}{dt}\right)} - \frac{dm_a}{dt} \cdot y(t) \quad (8)$$

where $(dm_a/dt) \cdot y(t)$ is the modulated component of the mass loss rate, with the underlying mass loss rate being $$\overline{\left(\frac{dm}{dt}\right)} = -m_0 \cdot \Delta\mu_r \cdot r(\bar{T}, t) \quad (9)$$

the intensity (or amplitude) of the modulation component of the mass loss rate being $$\frac{dm_a}{dt} = -m_0 \cdot \Delta\mu_r \cdot \left(\frac{\partial r}{\partial T}\right)_T T_a \quad (10)$$

and the modulated component of the mass change rate being $$\delta\left(\frac{dm}{dt}\right) = m_0 \Delta\mu_r \left(\frac{\partial r}{\partial T}\right)_T \delta T = \frac{dm_a}{dt} y(t) \quad (11)$$

Taking these derivations into consideration it is now possible to determine the apparent activation energy $E_\alpha$ utilizing any of the modulation functions mentioned above, in particular stochastic or event-controlled modulation functions.

The kinetics of a chemical reaction is often expressed by $$r = f(\alpha) \cdot k(T) \quad (12)$$

where $f(\alpha)$ is the temperature independent conversion function and $k(T)$ the rate constant.

The rate constant $k(T)$ is usually expressed by an Arrhenius equation with $k_0$ denoting the pre-exponential factor and E the activation energy $$k(T) = k_0 \exp\left(-\frac{E}{RT}\right) \quad (13)$$

The conversion function is temperature independent and comprises the reaction model. In the case of the so called model free kinetics no explicit reaction model is required. Instead, the reaction rate is described by a conversion dependent apparent activation energy $E(\alpha)$.

Here $E_\alpha$ is the average value of E in the temperature interval between $T-T_a$ and $T+T_a$. Taking into account the temperature independence of $f(\alpha)$ (isoconversional principle) as well as the conversion independence of $E_\alpha$ around T the temperature derivative $\partial r/\partial T$ of Equation (12) can now be expressed as $$\left(\frac{\partial r}{\partial T}\right)_T = r(\overline{T}) \frac{E_\alpha}{R\overline{T}^2} \quad (14)$$

where $E_\alpha$ is the apparent activation energy of the conversion at the underlying temperature $\overline{T}$.

In case of a periodic disturbance or modulation function the expression for the apparent activation energy $E_\alpha$ can now be derived by inserting Equation (14) into Equation (10), while considering only the intensity of the periodic components of Equations (9) and (10), as:

$$E_\alpha = -\left(\frac{dm_a}{dt}\right)\left(\overline{\frac{dm}{dt}}\right)^{-1} \frac{R\overline{T}^2}{T_a} \quad (15)$$

For the periodic case, the apparent activation energy curve $E_\alpha$ is mainly given by the ratio of the modulated mass loss intensity $dm_a/dt$ and the underlying mass loss rate $\overline{dm/dt}$. It has been shown, that Equation (15) yields more accurate results than Equation (2) for periodic modulation functions, such as sinusoidal modulation functions and that the linear approach is sufficient as long as the temperature modulation intensity $T_a$ is not too large, which limits the usability of purely periodic modulation functions.

In particular in view of the data evaluation the course of the modulation function rather than only its intensities should be analyzed. The large number of available data open the way for more suitable data evaluation procedures.

In order to evaluate the apparent activation energy $E_\alpha$ for such measurements Equation (15) has to be generalized by introducing the modulated component of the mass loss rate $\delta(dm(t)/dt)$ and temperature $\delta T(t)$ instead of the related intensities:

$$E(\alpha(t)) = -\frac{\partial\left(\frac{dm(t)}{dt}\right)}{\partial T(t)} R\overline{T}^2 \left(\overline{\frac{dm}{dt}}\right)^{-1} \quad (16)$$

The activation energy can now be directly derived by solving Equation (16) as almost continuous activation energy function $E(\alpha(t))$ in contrast to Equation (2) and allows e.g. the evaluation of large modulation intensities and/or the course of the modulation function.

Experimentally the apparent activation energy curve is mainly related to the ratio of the intensity of the modulated mass loss rate and the underlying mass loss rate. A TMTGA method, as explained in detail above, can be carried out with any of the mentioned modulation functions to determine the apparent action energy of the sample to be analyzed according to Equation (16), in particular with a stochastic or event-controlled modulation function.

Particularly advantageous is the use of a non-periodic modulation function for a TMTGA experiment. Principally the non-periodic modulation function can have any kind of shape, such as for example sequences of temperature ramps or steps or stochastic period and/or amplitude variations of sinusoidal functions.

All measurements using non-periodic modulation functions were carried out with a METTLER TOLEDO TGA/DSC 1 instrument with a SDTA sensor, said sensor additionally providing data on the sample temperature and the heat flow. For compatibility reasons all experiments were carried out with an underlying heating rate $\beta$ of about 2 K/min on a PTFE (polytetrafluoroethylene) sample with a mass of about 30 mg. The results were compared with conventional TGA measurements using the model free kinetics approach, which is implemented in the STARe software of METTLER TOLEDO.

Stochastic Modulation

The modulation function can principally be based on any shape, such as for example steps, ramps, etc., which can be described by a characteristic time of modulation $\tau$. For a stochastic modulation as example for a non-periodic modulation the characteristic time of modulation $\tau$ randomly fluctuates with time.

Here modulation functions comprising pulse sequences are discussed as exemplary modulation function having a pulse length $\tau$ as characteristic time of modulation, which is generated by a random number generator between the two limits $\tau_{min}$ and $\tau_{max}$. The lower limit $\tau_{min}$ is given by the time constant of the heat transfer from the furnace into the sample and the upper limit $\tau_{max}$ is given by the dynamic of a thermal event taking place.

Figure 2:
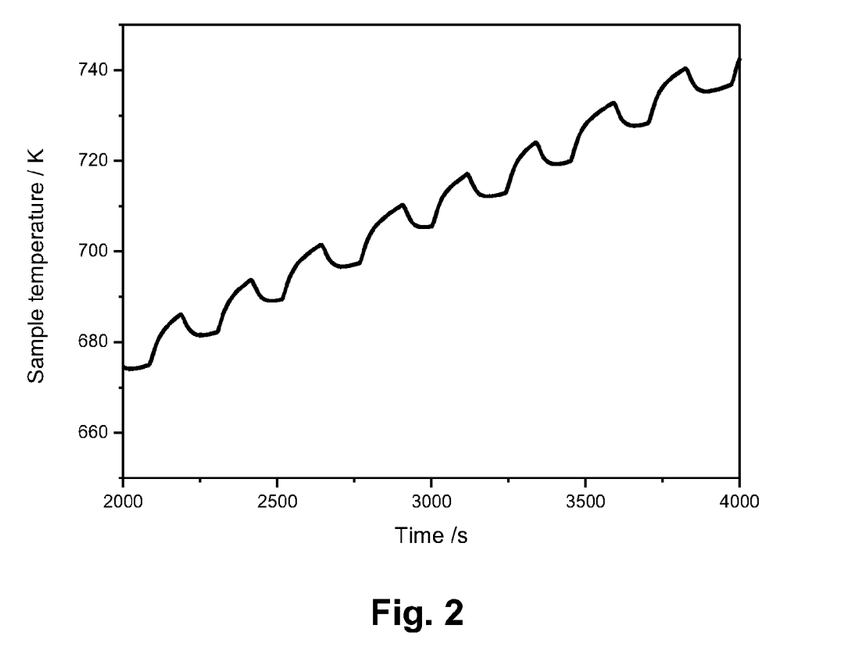
FIG. 2 which is a diagram showing a section of the sample temperature during a stochastic TMTGA measurement.

For the experiment the modulation time limits were selected to be $\tau_{min}=90$ s and $\tau_{max}=150$ s. The programmed step height (intensity of the modulation function) was $T_a=\pm 2.5$ K and the underlying heating rate was $\bar{\beta}=2$ K/min. From the resulting sample temperature curve shown in FIG. 2 it is evident that the sample temperature does not reach a steady state for the shorter pulses.

The simplest way of determining the functions $\delta T$ and $\overline{dm/dt}$ from the measured sample temperature and the mass loss curve comprises numerical derivation, smoothing and subtraction as described in more detail below.

Figure 3:
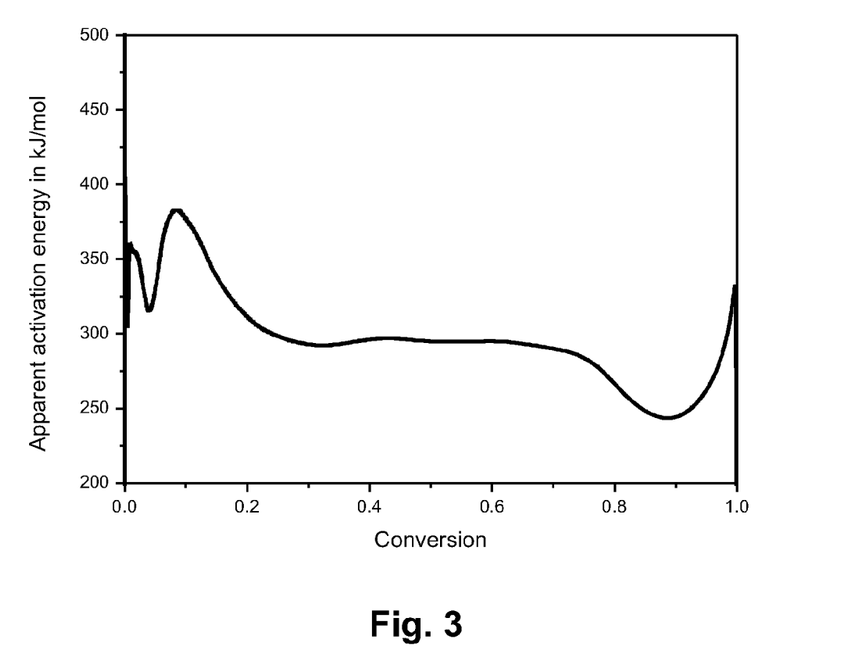
FIG. 3 which is a diagram showing the apparent activation energy as a function of conversion for a stochastic temperature modulation.

The resulting apparent activation energy curve derived from a TMTGA measurement with a stochastic modulation function, as example for a non-periodic modulation function, is shown in FIG. 3. The relatively large fluctuations of the activation energy curves in the conversion range below 0.2 are caused by the relatively small temperature fluctuation $T_{a,prog}$ of around 2.5 K. Higher values of $T_{a,prog}$ would increase the sensitivity of the measurement in this range.

The results can be further improved by solving Equation (16) through application of more stable mathematical procedures. Such mathematical procedures comprise besides others: signal analysis techniques based on integral transformations, such as Fourier- or Z-transformation, correlation analysis and/or parameter estimation methods. Suitable signal analysis techniques are disclosed for example in J. E. K. Schawe, et al. Thermochim. Acta 2006; 446: 147-155.

Event-Controlled Modulation

The known sinusoidal approach as well as the stochastic approach discussed above has the disadvantage that small intensities of the modulation component of the mass change rate $\delta(dm(t)/dt)$ in the temperature range of slow reactions lead to high fluctuations in the activation energy at small and large conversions. In order to minimize or even eliminate this effect it is desirable to use a modulation function with a high modulation intensity $T_a$ and a large characteristic modulation time $\tau$. A large $T_a$ increases the intensity of $\delta(dm(t)/dt)$. Increasing $\tau$ further increases the noise when using Equation (16) for the determination of the apparent activation energy due to the possibility to evaluate a larger number of data.

Further, the underlying mass change rate during the characteristic modulation time $\tau$ is relatively large at temperatures around the maximum reaction rate, which introduces large numerical errors in $E_\alpha$ determined by any of the Equations (2), (15) or (16). This can be overcome by minimizing $\tau$, which improves the separation of the underlying signal component and the modulation signal component. Furthermore, $T_a$ should be reduced as otherwise $\delta(dm(t)/dt)$ might violate the linear response conditions.

For an optimum measurement $\tau$ and $T_a$ should be large in the regions of low reaction rate and small in the region of high reaction rate.

This means that the behavior of the thermal event controls the parameters $\tau$ and $T_a$ of the temperature perturbation $\delta T(t)$. The criterion for the change of the temperature perturbation can be derived from the time or temperature dependency of the conversion and/or its derivatives. For event-controlled modulated function the native shape of a sample temperature pulse can for example be used to change $\tau$ and $T_a$ simultaneously.

Figure 4:
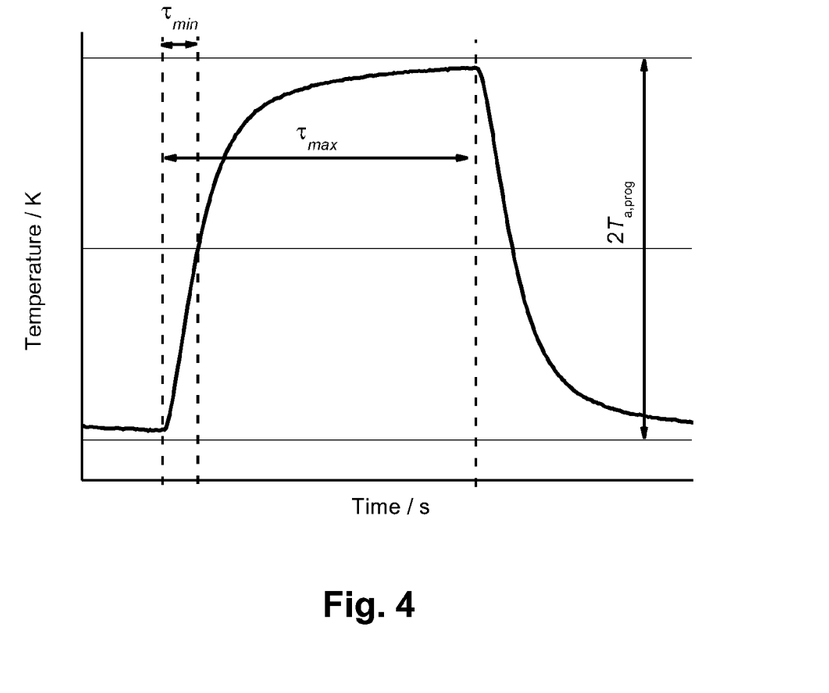
FIG. 4 which is a diagram showing the behavior of the sample temperature modulation functions for a pulse temperature modulation with a cycling time of $t_{max}$.

FIG. 4 shows the sample temperature response of a program temperature pulse. The peak flanks show exponential behavior. If the pulse length is long at $\tau_{max}$, the sample temperature reaches almost the steady state $T_a \approx T_{a,prog}$. By shortening the pulse length the reached maximum temperature decreases. At $\tau_{min}$ is $T_a \approx 0.5\, T_{a,prog}$. Consequently, as an effective choice of the pulse length $\tau$ in the range between $\tau_{min}$ and $\tau_{max}$ the pulse intensity $T_a$ changes accordingly. This means, if $\tau$ is controlled by a property of the thermal event, the pulse length and the pulse height of the modulation function are controlled simultaneously.

In accordance with the measuring equipment used the two limits were selected to be $\tau_{min}=20$ s and $\tau_{max}=180$ s.

The event control of T can be managed by using the reaction rate $r=d\alpha/dt$ or the time derivative of the reaction rate $v=dr/dt$. Here v is used immediately after the temperature jump, normalized by the programmed pulse intensity $|v/T_{a,prog}|$. v can be estimated from the mass change during ca. the first 10 s after the temperature jump in the program temperature:

$$v = \frac{\Delta m_1 - \Delta m_2}{m_0 \Delta t^2} \quad (17)$$

where $\Delta t$ is a time interval of ca. 5 s, $m_0$ the initial sample mass, $\Delta m_1$ the slope calculated by linear fitting of the measured sample mass during ca. the first 5 s after the temperature jump and $\Delta m_2$ the related value for the time period between about 5 s and 10 s after the jump. A criterion for the cycling time could be $$\tau = \begin{cases} \tau_{max} & \text{if } |v/T_{a,prog}| \leq c_{min} \\ a + b\log(|v/T_{a,prog}|/\text{ms}^2 K^{-1}) & \text{if } c_{min} < |v/T_{a,prog}| < c_{max} \\ \tau_{min} & \text{if } |v/T_{a,prog}| \geq c_{max} \end{cases} \quad (18)$$

The constants $c_{min}$ and $c_{max}$ define the ranges in which $\tau$ changes between $\tau_{min}$ and $\tau_{max}$. Pre-experiments show that $c_{min}=0.12$ ms² K⁻¹ and $c_{max}=0.60$ ms² K⁻¹ are suitable limits for $|v/T_{a,prog}|$. Because of the exponential slope of the pulse flanks $\tau$ should be changed logarithmically in between the limits. The parameters a and b have been determined to be $a=-30.8$ s and $b=-228.9$ s from the conditions at the interval limits:

$$b = \frac{\tau_{max} - \tau_{min}}{\log(\tau_{min}/c_{max})} \quad (19)$$

$$a = \tau_{max} - b\log\left(\frac{c_{min}}{\text{ms}^2 K}\right) \quad (20)$$

and $T_{a,prog}$ and $\bar{\beta}$ were selected to be 2.5 K and 2 K min, respectively.

Figure 5:
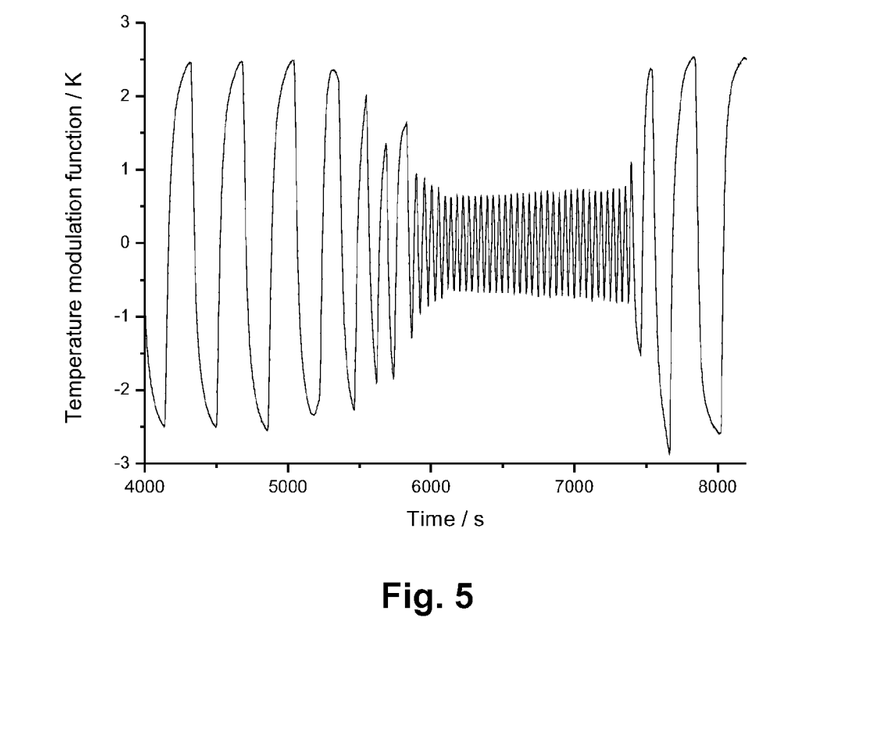
FIG. 5 a diagram showing a section of the temperature modulation function $\delta T(t)$ for an event-controlled experiment according to Equation (18)
Figure 6:
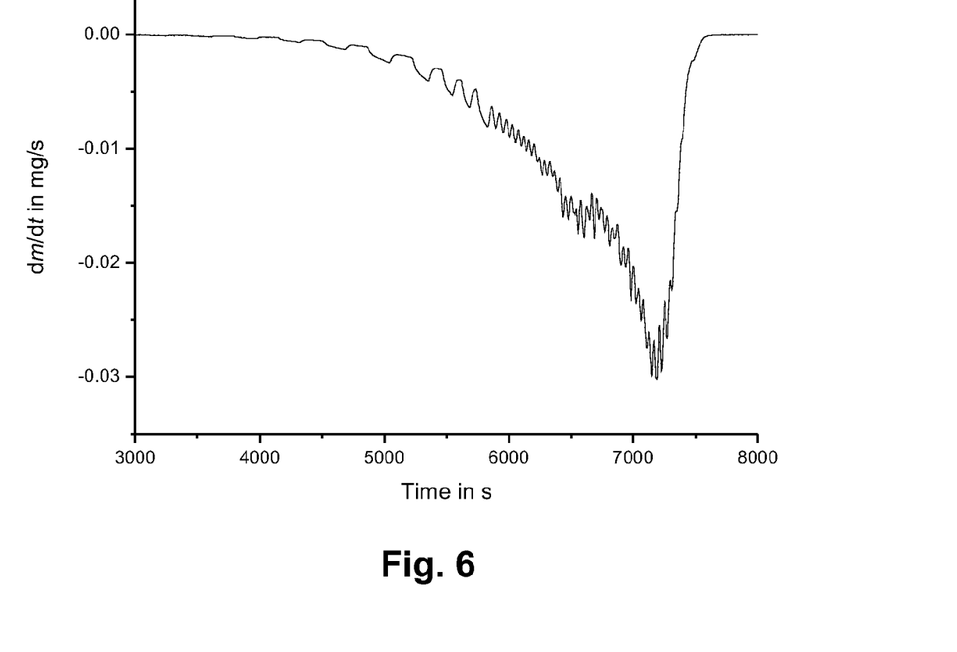
FIG. 6 which is a diagram showing the first derivative of the mass loss curve measured using the event-controlled temperature modulation function according to FIG. 5.

FIG. 5 shows a section of the measured modulation function $\delta T$ for said experiment and the measured mass loss rate $(dm/dt)(t)$ (DTG curve) is displayed in FIG. 6. The resulting apparent activation energy curve is plotted in FIG. 7. This curve shows lower fluctuations in the activation energy curve at low conversions compared to the other methods. The apparent activation energy is almost constant at conversions above 0.7.

The resulting activation energy can again be further improved by optimizing the computing procedure as discussed in relation to the non-periodic temperature modulation.

Figure 7:
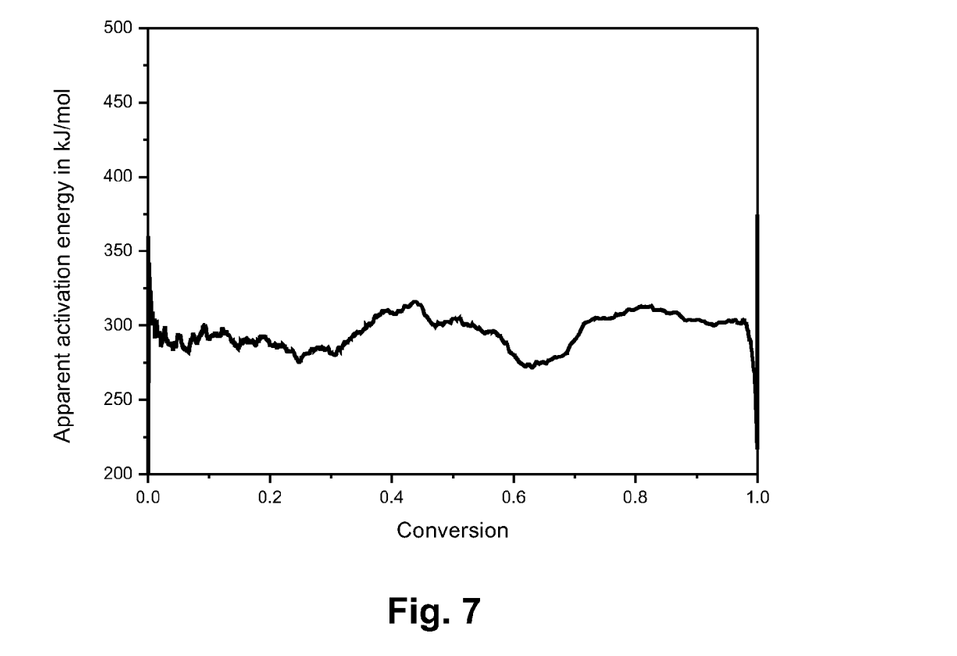
FIG. 7 which is a diagram showing the apparent activation energy as a function of conversion for an event-controlled modulation.

The results presented in FIGS. 5, 6 and 7 clearly show that the event-controlled modulation minimizes evaluation errors.

The determination of $E_\alpha$ using Equation (18) can be further improved by determining the sample temperature through a direct measurement, as it is e.g. possible with the setup including a SDTA sensor as describe above.

Based on the assumption that the temperature fluctuation due to the modulation function is a small disturbance of the course of reaction a new simplified TMTGA method has been developed. The method according to the invention can be used to determine the apparent activation energy of a reaction directly as a function of conversion. The function can also be used to predict the course of reaction under different conditions and it could be shown that it is very robust regarding experimental uncertainties.

Further the method according to the invention is independent of the type of temperature modulation. The temperature modulation is limited with regard to the temperature change during a modulation cycle and the characteristic modulation time $\tau$ of said temperature change. In case of a periodic temperature modulation function $\tau$ is the period of said function.

The lower limit of $\tau$ is related to the heat transfer conditions in the TGA experiment. $\tau$ has to be large enough so that the sample temperature changes due to the modulation of the furnace temperature. On the other hand $\tau$ has to be small enough so that there are sufficient temperature changes during the course of reaction. The signal to noise ratio can be significantly improved using a long modulation time $\tau$.

In order to include the essentially whole reaction time into the TMTGA method, a long modulation time $\tau$ should be used at the beginning and near the end of the reaction, as the reaction rate is low then. Advantageously, this can be achieved by using a modulation function which is controlled by the thermal event of the sample as described above, which increases the accuracy of the resulting apparent activation energy, respectively the activation energy function, significantly.

As described in detail above, using a non-periodic modulation functions allows the determination of the related data, e. g. $\bar{r}$, $\bar{r}_a$, $\bar{T}$ and $T_a$, directly from the measured TMTGA curves and/or by other more advanced signal evaluation techniques, such as techniques used e.g. in relation to stochastic TMDSC. The accuracy of the results can further be improved by using advanced evaluation techniques.

Further the underlying heating rate $\bar{\beta}$ can be varied or controlled in particular in the region of the maximum reaction rate in order to enhance the resulting resolution.

The event (or sample) controlled temperature modulation technique is particularly advantageous as it can significantly improve the quality of the activation energy curve in one single measurement due to the optimization of resolution and sensitivity.

What is claimed is:

1. A method for analyzing a sample using a temperature-modulated thermogravimetric analysis (TMTGA), wherein the method comprises the steps of:
    placing a sample on a measuring position in a thermogravimetric analysis (TGA) instrument that comprises a furnace arranged in a furnace housing, an electronic balance with a load receiver arranged in a balance housing so that the load receiver extends into the furnace housing with the measuring position being arranged at one end of the load receiver within the furnace housing, and a control unit for controlling at least one of the balance and the furnace;
    subjecting the sample to a temperature program provided by the control unit, which varies the temperature of the furnace;
    measuring, with the electronic balance, a change of the mass (m(T,t)) of the sample as a function of time while the sample is subjected to the temperature program; and;
    using the measured mass change to determining at least one kinetic parameter of the sample;
    wherein the temperature program provides temperature-time setpoints for controlling the sample temperature (T(t)) as determined by the formula:

$$T(t)=\bar{T}(t)+\delta T(t)$$

where $\bar{T}(t)$ represents an underlying temperature change superimposed by a temperature perturbation ($\delta T(t)$) with a characteristic time of modulation ($\tau$); and
    wherein the temperature program is one or both of a stochastic program and an event-controlled program.

2. The method of claim 1, further comprising the step of determining the sample temperature as a function of time using a temperature sensor arranged in the vicinity of the measurement position.

3. The method of claim 1, wherein:
    the temperature program includes at least a stochastic program; and
    the characteristic time of modulation of the stochastic temperature perturbation fluctuates randomly.

4. The method of claim 3, wherein:
    the stochastic temperature perturbation comprises pulse sequences, each having a pulse length that represents the characteristic time of modulation, each pulse length generated by a random number generator to be between a predetermined minimum and a predetermined maximum.

5. The method of claim 1, wherein:
    the temperature program includes at least a stochastic program; and
    the temperature program varies an intensity of the stochastic temperature perturbation.

6. The method of claim 1, wherein:
    the temperature program includes at least an event-controlled program; and
    the temperature program modulates the event-controlled temperature perturbation by modulating at least one of:
        the characteristic time of modulation, and
        the temperature modulation intensity,
    in relation to changes in at least one of:
        the mass,
        the conversion of the mass, and
        derivatives thereof,
    during a TGA experiment.

7. The method of claim 1, further comprising the step of adapting an underlying heating rate of the temperature program.

8. The method of claim 1, further comprising the step of providing, from the temperature program, non-periodic temperature-time data for controlling the sample temperature.

9. The method of claim 1, further comprising the step of using the mass change of the sample as a function of time and temperature that are measured in a single TGA measurement to determine the at least one kinetic parameter.

10. The method of claim 1, further comprising the steps of:
    determining, from a TGA test-measurement of the sample, the parameters of the temperature perturbation;

performing a TMTGA measurement by measuring at least one like sample with the TGA instrument, using a temperature program comprising the temperature perturbation with the previously determined parameters; and determining at least one kinetic parameter of the sample from the TMTGA measurement.

11. The method of claim 1, further comprising the step of determining the apparent activation energy as a kinetic parameter.

12. A thermogravimetric analysis (TGA) instrument for carrying out a temperature-modulated thermogravimetric analysis (TMTGA), the instrument comprising:

a furnace arranged in a furnace housing;

an electronic balance having a load receiver arranged in a balance housing, such that one end of the load receiver extends into the furnace housing and comprises a measuring position for receiving a sample;

a control unit that controls the operation of at least one of the electronic balance and the furnace, the control unit including a temperature program that controls the temperature of the furnace;

wherein the electronic balance measures changes in the mass of the sample as a function of time and temperature while the sample is being subjected to the temperature program;

wherein the control unit comprises means for determining at least one kinetic parameter of the sample by analyzing the sample's changes in mass over time and temperature; and wherein the temperature program is one or both of a stochastic and event-controlled temperature program that provides temperature-time setpoints for controlling the sample temperature (T(t)) and produces an underlying temperature change ($\overline{T}(t)$) that is superimposed by a temperature perturbation ($\delta T(t)$) with a characteristic time of modulation ($\tau$) according to the equation:

$$T(t)=\overline{T}(t)+\delta T(t).$$

13. The instrument of claim 12, further comprising a temperature sensor arranged in the vicinity of the measurement position for measuring the sample temperature.

14. The instrument of claim 12, wherein the at least one kinetic parameter is the apparent activation energy.

15. A method for analyzing a sample using a temperature-modulated thermogravimetric analysis (TMTGA), wherein the method comprises the steps of:

placing a sample on a measuring position in a thermogravimetric analysis (TGA) instrument that comprises a furnace arranged in a furnace housing, an electronic balance with a load receiver arranged in a balance housing so that the load receiver extends into the furnace housing with the measuring position being arranged at one end of the load receiver within the furnace housing, and a control unit for controlling at least one of the balance and the furnace;

subjecting the sample to an event-controlled temperature program provided by the control unit, which varies the temperature of the furnace;

measuring, with the electronic balance, a change of the mass (m(T,t)) of the sample as a function of time while the sample is subjected to the temperature program; and;

using the measured mass change to determining at least one kinetic parameter of the sample;

wherein the temperature program provides temperature-time setpoints for controlling the sample temperature (T(t)) as determined by the formula:

$$T(t)=\overline{T}(t)+\delta T(t)$$

where $\overline{T}(t)$ represents an underlying temperature change superimposed by a temperature perturbation ($\delta T(t)$) with a characteristic time of modulation ($\tau$); and wherein the temperature program modulates the event-controlled temperature perturbation by modulating at least one of:
the characteristic time of modulation, and
the temperature modulation intensity,
in relation to changes in at least one of:
the mass,
the conversion of the mass, and
derivatives thereof,
during a TGA experiment.

16. The method of claim 15, further comprising the step of determining the sample temperature as a function of time using a temperature sensor arranged in the vicinity of the measurement position.

17. The method of claim 15, further comprising the step of adapting an underlying heating rate of the temperature program.

18. The method of claim 15, further comprising the step of providing, from the temperature program, non-periodic temperature-time data for controlling the sample temperature.

19. The method of claim 15, further comprising the step of using the mass change of the sample as a function of time and temperature that are measured in a single TGA measurement to determine the at least one kinetic parameter.

20. The method of claim 1, further comprising the steps of:

determining, from a TGA test-measurement of the sample, the parameters of the temperature perturbation;

performing a TMTGA measurement by measuring at least one like sample with the TGA instrument, using a temperature program comprising the temperature perturbation with the previously determined parameters; and determining at least one kinetic parameter of the sample from the TMTGA measurement.

21. The method of claim 15, further comprising the step of determining the apparent activation energy as a kinetic parameter.

* * * * *